(12) United States Patent
Miyaji et al.

(10) Patent No.: US 7,134,873 B2
(45) Date of Patent: Nov. 14, 2006

(54) ORTHODONTIC WIRE LIGATING MEMBER

(75) Inventors: Hiroaki Miyaji, Ohtawara (JP); Kazuo Machida, Ohtawara (JP); Hajime Tamura, Tokyo-to (JP)

(73) Assignee: Dentsply-Sankin K. K., Tochigi (JP)

( * ) Notice: Subject to any disclaimer, the term of this patent is extended or adjusted under 35 U.S.C. 154(b) by 0 days.

(21) Appl. No.: 10/819,301

(22) Filed: Apr. 7, 2004

(65) Prior Publication Data

US 2004/0209219 A1    Oct. 21, 2004

(30) Foreign Application Priority Data

Apr. 18, 2003    (JP)    ............................ 2003-114389

(51) Int. Cl.
*A61C 7/00*    (2006.01)
(52) U.S. Cl. ..................................................... 433/10
(58) Field of Classification Search .................. 433/10, 433/11, 13, 15, 16, 8, 9, 14
See application file for complete search history.

(56) References Cited

U.S. PATENT DOCUMENTS

| 4,038,753 A | 8/1977 | Klein |
| 4,551,094 A * | 11/1985 | Kesling ........................... 433/8 |
| 4,950,158 A | 8/1990 | Barngrover et al. |
| 5,470,228 A * | 11/1995 | Franseen et al. ................ 433/8 |
| 5,711,666 A | 1/1998 | Hanson |
| 5,857,849 A * | 1/1999 | Kurz ............................ 433/10 |
| 6,142,775 A * | 11/2000 | Hansen et al. .................. 433/8 |
| 6,168,429 B1 | 1/2001 | Brown |
| 6,659,766 B1 | 12/2003 | Abels et al. |

FOREIGN PATENT DOCUMENTS

EP    0 623 320 A1    11/1994

* cited by examiner

*Primary Examiner*—Melba Bumgarner
(74) *Attorney, Agent, or Firm*—Rader, Fishman & Grauer PLLC (57) ABSTRACT

An orthodontic wire ligating member is engageable with an orthodontic bracket to retain an archwire inserted into a groove in the bracket. The ligating member is an elastically deformable member made of a synthetic resin and has at least two spaced engaging portions detachably engageable with the bracket, and a back portion integral with the engaging portions and elastically deformable flexibly to engage the bracket to retain the archwire. Thus, the friction between the archwire and the bracket slot is minimized, and the archwire is retained in a friction-free or low-friction state.

6 Claims, 7 Drawing Sheets

ORTHODONTIC WIRE LIGATING MEMBER

BACKGROUND OF THE INVENTION

1. Field of the Invention

The present invention relates to an orthodontic wire ligating member for use in orthodontic treatment. More particularly, the present invention relates to an orthodontic wire ligating member made of a synthetic resin and engaged with a bracket to retain an archwire.

2. Description of the Related Art

Orthodontic treatment methods using brackets, tubes, etc. to correct a row of improperly positioned teeth are well known. In a typical orthodontic method, brackets, for example, are bonded to teeth to shift the positions of the teeth gradually by applying thereto mechanical tension, i.e. pushing force, pulling force, twisting or other elastic restoring force, with an archwire attached to the brackets, thereby correcting the malpositioned teeth. In this treatment method, each bracket has a slot for engagement with an archwire formed in the center of the bracket body. In addition, wings are provided on the outside of the bracket body. After being inserted into the slot, the archwire is held in the slot by using a ligating device that is mounted in engagement with the wings.

As the ligating device, for example, a ligature wire (ligating wire) of stainless steel, an O-ring of polyurethane, or a ligating module is used to ligate the archwire to the bracket. When the ligature wire, O-ring or ligating module is fitted or replaced, a force of not less than 2 to 3 N (Newtons) is applied to the tooth in the form of vibration. This inflicts pain on the patient.

Figure 18:
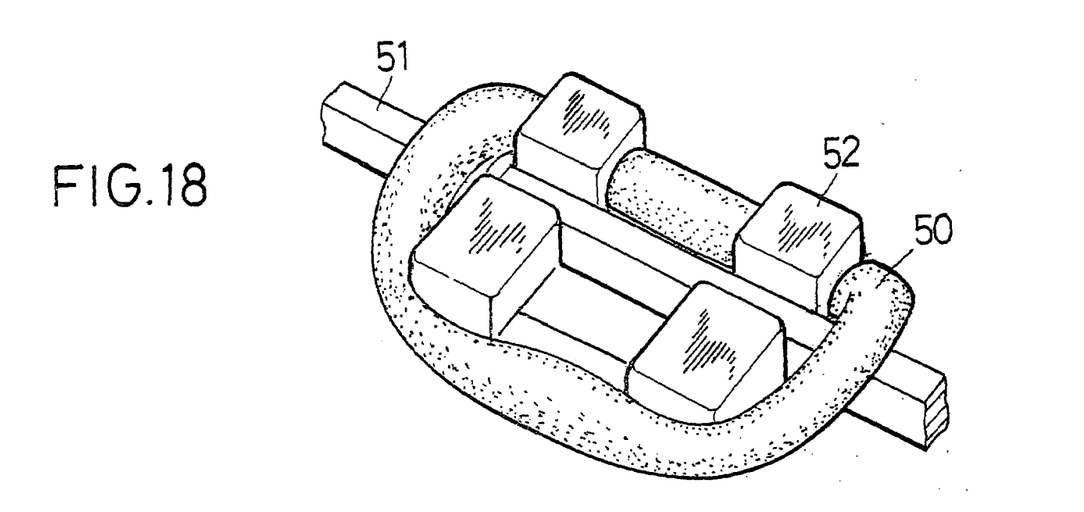
FIG. 18 is an external view showing a way in which an O-ring made of an elastic material is wound around wings of a bracket to ligate an archwire in a conventional device.

FIG. 18 shows a conventional example in which an O-ring 50 made of an elastic material is used to ligate an archwire 51 to a bracket 52. In this ligation example, the O-ring 50 is mounted by being wound around the wings of the bracket 52 to retain the archwire 51 on the bracket 52 by elastic force.

The ligating method using a ligature wire is a method that has heretofore generally been used. With this method, the ligature wire is gripped by using the tip of a pair of pliers selected according to each particular application, and the wire is wound around the bracket by manipulating the pliers to thereby ligate the archwire to the bracket. These days, however, O-rings made of silicone rubber or a thermoplastic synthetic resin elastomer, e.g. polyurethane, are frequently used as disclosed, for example, in the specifications of U.S. Pat. Nos. 4,038,753 and 4,950,158.

European Publication No. 0 623 320 A1 and the specification of U.S. Pat. No. 5,711,666 disclose techniques relating to self-ligating orthodontic brackets that allow an archwire to be ligated with a simple operation. The former of the two techniques uses a slide member that is slidable to cap the archwire. The latter technique uses a ligating member having a spring effect to ligate the archwire.

In orthodontic treatment, teeth are gradually moved by applying forces thereto in three-dimensional directions using orthodontic appliances such as brackets, wires, etc. To effect efficient tooth movement, it is better to move teeth with an archwire that is retained in such a manner as to be slidable in a friction-free state (i.e. a state where friction can be minimized in the present invention) where unnecessary friction between the archwire and the brackets is minimized when forces required for orthodontics are generated, or in a low-friction state. With the conventional ligating methods using a metal wire, rubber, etc., the archwire is held down to the bracket slot surface with an excessive pressing force. Consequently, static friction, shearing stress by the archwire, etc. occur besides corrective forces required for the tooth movement physiologically. These unnecessary forces make it difficult to effect the desired tooth movement.

Accordingly, as the orthodontic treatment progresses, improper force other than force necessary for the movement of the patient's teeth acts. This gives a foreign body sensation to the patient, irritates the mucous membrane of the mouth, and inflicts orthodontic pain on the patient during the treatment. The technique that uses a self-ligating bracket solves the above-described problems. However, the bracket has a large and complicated structure because it comprises a slide member, a spring member, etc. Further, there are cases where a special-purpose tool is needed to attach and detach the slide member or the spring member to and from the bracket. Accordingly, the orthodontist is required to have proficient skill in ligating.

Moreover, the foregoing conventional ligating methods are unhygienic because food and plaque are likely to be left on the orthodontic appliances. In regard to configuration, the ligating members have a configuration with many projections and recesses. Therefore, the conventional methods have a problem in terms of aesthetics. Accordingly, there is a demand for a ligating technique that inflicts minimal corrective pain on the patient and allows ligating to be effected easily with a simple arrangement.

SUMMARY OF THE INVENTION

The present invention was made in view of the above-described technical background to attain the following objects.

An object of the present invention is to provide an orthodontic wire ligating member that allows an archwire to be easily ligated to a bracket and a tube with a simplified ligating structure.

Another object of the present invention is to provide an orthodontic wire ligating member that allows tooth movement in a friction-free state (i.e. a state where friction can be minimized in the present invention) or in a low-friction state, so that the desired tooth movement is effected rapidly and thus the period of time for orthodontic treatment is shortened.

Still another object of the present invention is to provide an orthodontic wire ligating member that allows tooth movement to be effected with a small corrective force, thereby minimizing pain inflicted on the patient.

A further object of the present invention is to provide an orthodontic wire ligating member having an archwire retaining structure with a minimum of unevenness and a smoothly curved external configuration to improve aesthetics.

A still further object of the present invention is to provide an orthodontic wire ligating member capable of being easily attached and detached to and from even existing conventional brackets.

An advantage of the orthodontic wire ligating member according to the present invention is that an orthodontic system using the ligating member is easy to clean, and bits of food are unlikely to be left thereon.

Another advantage of the orthodontic wire ligating member according to the present invention is that because there is no end of cut wire as experienced with the conventional wire ligating device, the sense of incongruity and irritation in the mouth are minimized, and cleanliness is improved.

Still another advantage of the orthodontic wire ligating member according to the present invention is that because tooth movement can be effected with a small corrective force, it is possible to use orthodontic elastic members, such as an archwire and an elastic chain, smaller in diameter or wall thickness than the existing products.

A further advantage of the orthodontic wire ligating member according to the present invention is that dirt on the ligating member is less inconspicuous and deterioration of the ligating member is less than in the case of the conventional O-rings and ligating modules made of synthetic resin elastomers.

To realize the above-described objects and advantages, the present invention adopts the following arrangements.

An orthodontic wire ligating member according to the present invention is engageable with an orthodontic bracket to retain an archwire inserted into a groove in the bracket.

The ligating member is an elastically deformable member made of a synthetic resin and has at least two spaced engaging portions detachably engageable with the bracket, and a back portion integral with the two engaging portions and elastically deformable flexibly to engage the bracket to retain the archwire.

Preferably, the back portion has a wire keeper formed integral with the back portion and inserted into the groove to hold the archwire.

Preferably, the synthetic resin is at least one selected from the group consisting of polyamides, polyacetals, and polycarbonates, and has a tensile break strength of not less than 55 MPa, a bending strength of not less than 80 MPa, a modulus in flexure of not less than 2500 MPa and an impact value of not less than 50 J/m.

Preferably, the engaging portions are provided with projections extending along the longitudinal direction of the archwire. The projections are engageable with respective recessed portions of the bracket. Preferably, the engaging portions are provided with projections extending in a direction perpendicular to the longitudinal direction of the archwire. The projections are engageable with respective recessed portions or holes of the bracket. Further, it is preferable that a surface of the bracket that is approximately parallel to a joint surface thereof that is to be bonded to a tooth surface should have a curved surface configuration.

The bracket that can use the orthodontic wire ligating member according to the present invention may be a buccal tube having a through-hole that allows the archwire to extend therethrough. Further, the archwire may be made of a nickel-titanium alloy for orthodontics and may have a diameter of from 0.20 mm. to 0.35 mm. Further, it is preferable aesthetically that the bracket should be elliptical as viewed in a direction normal to the joint surface to be bonded to a tooth surface.

Further, the engaging portions of the ligating member may be branched to engage the bracket. Further, a polyurethane elastic chain to be engaged with the bracket preferably has a wall thickness of from 0.2 mm to 0.3 mm.

The above and other objects, features and advantages of the present invention will become more apparent from the following description of the preferred embodiments thereof, taken in conjunction with the accompanying drawings.

DESCRIPTION OF THE PREFERRED EMBODIMENTS

Figure 1:
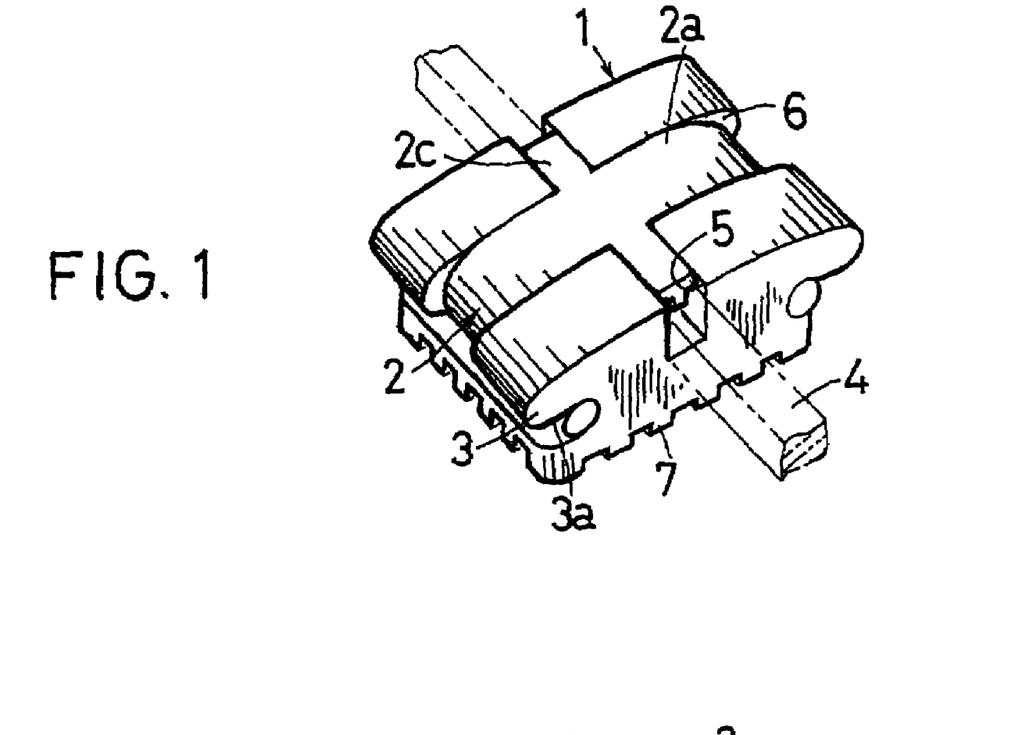
FIG. 1 is an external view showing an orthodontic wire ligating member according to the present invention as applied to a twin-type bracket.
Figure 2:
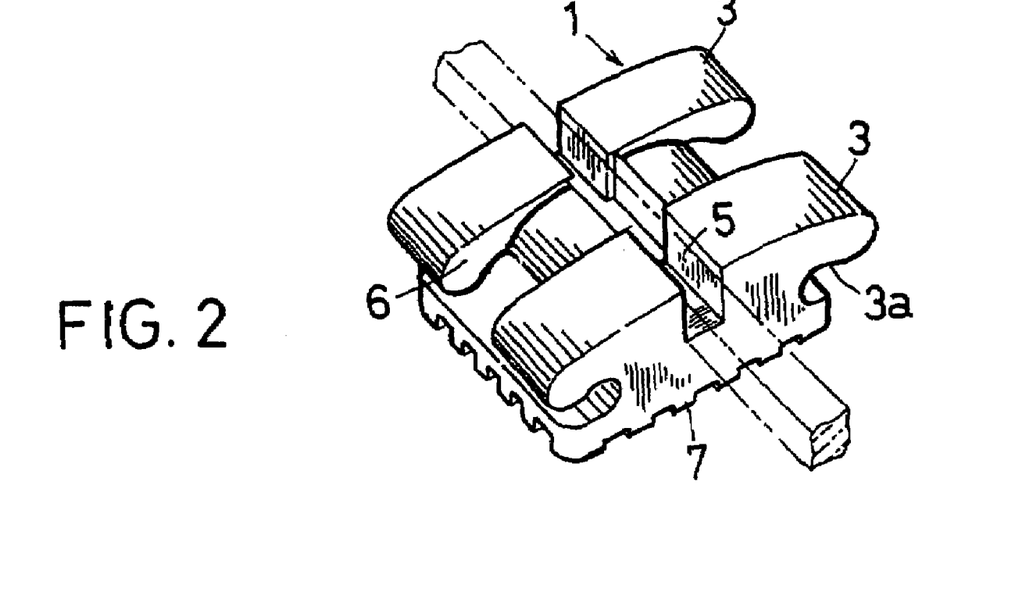
FIG. 2 is an external view showing the twin-type bracket in the state of being a single element.

Embodiments of the present invention will be described below with reference to the accompanying drawings. FIG. 1 is an external view showing an embodiment of the orthodontic wire ligating member according to the present invention, in which it is used in a twin-type bracket 1. FIG. 2 is an external view showing only the bracket 1. The orthodontic wire ligating member 2 is used by being mounted on the bracket 1 as shown in FIG. 1. The bracket 1 shown in FIG. 1 is a twin-type bracket made of a transparent synthetic resin, which has two pairs of wings 3 disposed parallel to each other, i.e. four projecting portions (portions projecting outward like eaves). The bracket 1 has in the center thereof a U-groove shaped slot 5 for retaining an archwire 4 extending therethrough, i.e. a groove in which the archwire 4 is slidably inserted.

Regarding the bracket 1, a large number of different types of brackets are known, such as single-type brackets and archwire-guiding metallic groove members having extended portions. The orthodontic wire ligating member 2 according to this embodiment will be described below by way of an example in which it is applied to the above-described twin-type bracket 1. However, the orthodontic wire ligating member 2 is also applicable to existing conventional brackets having other configurations. Further, the orthodontic wire ligating member 2 is applicable to any type of existing brackets irrespective of the constituent material, e.g. metal brackets, plastic brackets, and ceramic brackets. The orthodontic wire ligating member 2 is also applicable to a buccal tube for use in the molar region, as will be described later.

With regard to the bracket 1, there are various types of brackets differing slightly in configuration according to the site of a tooth to which the bracket 1 is to be attached, e.g. those for incisors, canines, and premolars. The bracket 1 may vary in torque, angulation, etc. and differ in configuration according to the orientation of a tooth to be corrected. There are known various brackets designed in conformity to these circumstances. Basically, the bracket 1 is provided in the center thereof with a slot 5 for passing an archwire 4 therethrough and has wings 3 for ligating provided on the side walls thereof.

The bracket 1 may be provided with a hook, depending on the type. The lower side of the bracket 1 is a joint surface 7 to be bonded to a tooth. The joint surface 7 is bonded to the tooth surface through an adhesive. The basic structure and function of the bracket 1 body are publicly known and not directly concerned with the gist of the present invention. Therefore, a detailed description thereof is omitted. Conventionally, a thin stainless steel wire (ligating wire or ligature wire) is used to support the inserted archwire 4 on the bracket 1 and wound around the wings 3. In the conventional method using an O-ring, also, the O-ring is engaged with the wings 3 to support the archwire 4 in the slot 5 of the bracket 1.

The feature of the ligating member 2 in this embodiment resides in that the archwire 4 is not securely held in the slot 5 but movably supported in the slot 5 and further made easily slidable. The feature of this embodiment also resides in the structure and function of the ligating member 2 for slidably retaining the archwire 4 as stated above. The orthodontic wire ligating member 2 is a molded piece made of a synthetic resin. The material of the synthetic resin is a so-called engineering plastic.

The engineering plastic is at least one selected from the group consisting of polyamides, polyacetals, polycarbonates, etc. A material for the bracket 1 may be selected according to each particular use application. Optimal characteristic values of the engineering plastic used in this embodiment are as follows. The tensile break strength is not less than 55 MPa. The bending strength is not less than 80 MPa. The modulus in flexure is not less than 2500 MPa. The impact value is not less than 50 J/m.

Next, an orthodontic wire ligating member 2 as an embodiment of the present invention will be described in detail. FIG. 2 is an external view showing a twin-type bracket 1 in the state of being a single element. The bracket 1 is provided in the center thereof with a slot (wire insertion groove) 5 for retaining an archwire 4. Further, the bracket 1 is provided on both sides thereof with two pairs of wings 3, i.e. four projecting portions, projecting parallel to each other from the center thereof in a direction crossing the slot 5. The lower portion 3a of each wing 3 is recessed in a U shape. A groove 6 is provided between two pairs of wings 3. A joint surface 7 that is to be bonded to a tooth surface is made uneven with recesses and projections to increase the adhesion to the tooth surface.

Figure 3:
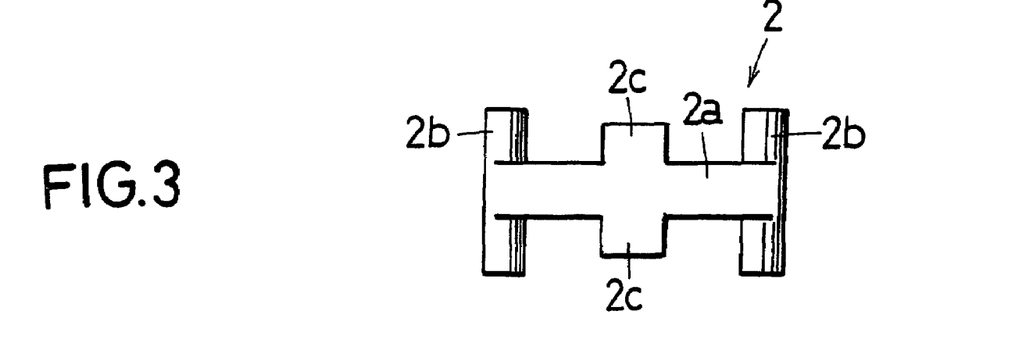
FIG. 3 is a front view of the ligating member shown in FIG. 1.
Figure 4:
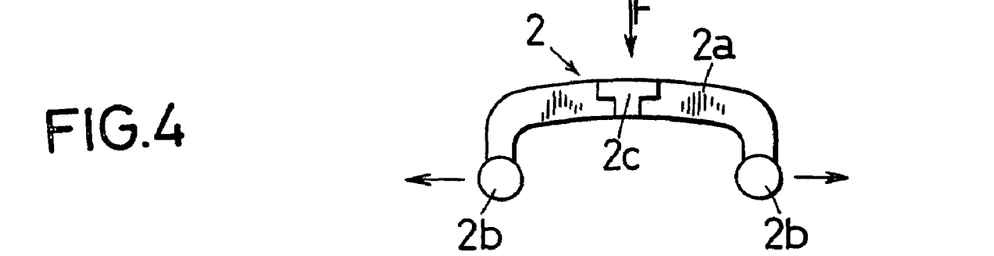
FIG. 4 is a side view of FIG. 3.

Meanwhile, the ligating member 2 is shown in FIGS. 3 and 4. FIG. 4 is a side view of FIG. 3. The ligating member 2 is molded of a thermoplastic synthetic resin. The ligating member 2 comprises a back portion 2a, leg portions 2b and a wire keeper 2c. The leg portions 2b are disposed at both ends of the back portion 2a. The wire keeper 2c is disposed at the center of the back portion 2a. The leg portions 2b and the wire keeper 2c are disposed to extend parallel to each other and connected together as one unit by the back portion 2a, which is disposed to lie on the longitudinal centers of the leg portions 2b and the wire keeper 2c.

In other words, the ligating member 2 has a structure in which the leg portions 2b and the wire keeper 2c project bilaterally with respect to the back portion 2a, which is a center member. That is, the ligating member 2, as seen in a front view, is substantially in the shape of two English letter E's placed back to back in axial symmetry (see FIG. 3). The leg portions 2b are engageable with the lower portions 3a of the wings 3 of the bracket 1 as shown in FIG. 1. As has been stated above, the back portion 2a is integrally formed with the wire keeper 2c extending in a direction crossing the back portion 2a. The wire keeper 2c is a portion that is inserted into the slot 5 of the bracket 1.

The lower surface of the wire keeper 2c is positioned over the upper surface of the archwire 4. Therefore, the spacing between the wire keeper 2c and the archwire 4 can be adjusted by varying the thickness of the wire keeper 2c. That is, in the initial stage of orthodontic treatment, the thickness of the wire keeper 2c is set to form a gap between the wire keeper 2c and the archwire 4 so that the lower surface of the wire keeper 2c does not contact the upper surface of the archwire 4. Consequently, the friction between the wire keeper 2c and the archwire 4 is minimized. Accordingly, it is possible to create a state where the archwire 4 is easily slidable freely in the slot 5.

In the intermediate and final stages of orthodontic treatment, no large tooth movement is needed. Therefore, the thickness of the wire keeper 2c is set so that the lower surface of the wire keeper 2c contacts the upper surface of the archwire 4. The contact between the wire keeper 2c and the archwire 4 allows the torque of the archwire 4 to be transmitted to the bracket 1 effectively and hence enables the effect of the treatment to be improved advantageously. The ligating member 2 is elastically deformable. Accordingly, if a force F is externally applied to the ligating member 2 with a finger, for example, as shown in FIG. 4, the leg portions 2b are forced to extend outward as shown by the two arrows. Removing the finger from the ligating member 2 allows the leg portions 2b to return to the original shape.

Accordingly, the ligating member 2 can be incorporated into the bracket 1 by pushing the former into the latter in one stroke with only a fingertip or a simple pushing tool by utilizing elastic deformation of the ligating member 2. When the ligating member 2 is to be removed from the bracket 1, the back portion 2a of the ligating member 2 is cut with a cutter to remove the ligating member 2. The removed ligating member 2 is discarded. The ligating member 2 is a small-sized molded piece and a simple and low-cost component. Therefore, it is handled as an expendable component. Usually, the ligating member 2 is not molded in the form of a single element but integrally molded in the form of a continuous structure for 20 teeth per patient, for example.

Figure 5:
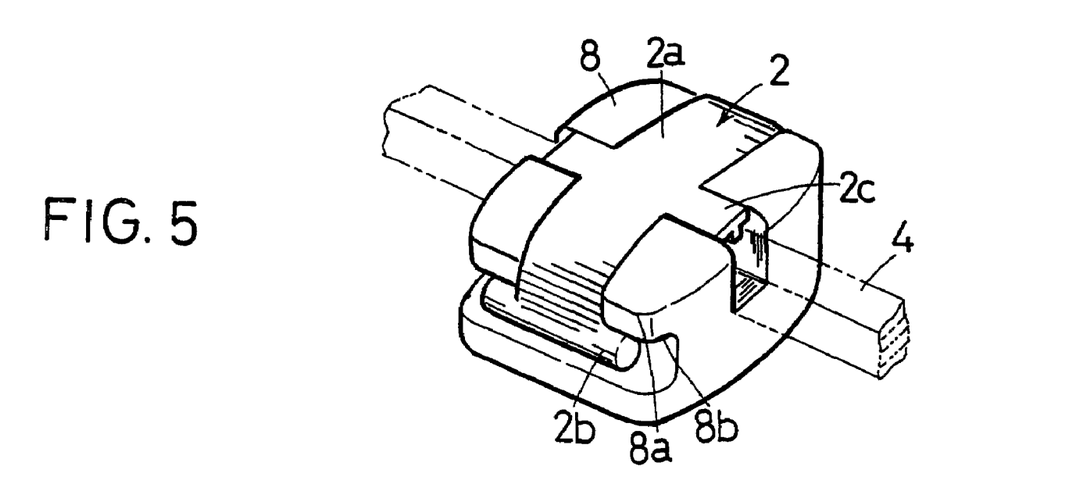
FIG. 5 is an external view showing the orthodontic wire ligating member as applied to a bracket different in configuration from that shown in FIG. 1.

FIG. 1 is an external view of the orthodontic wire ligating member 2 as fitted to an existing bracket 1. In contrast, FIG. 5 shows an example in which the external configuration of the bracket 1 is altered into a smoothly curved configuration. Because the bracket 8 is bonded to the tooth surface, bits of food are likely to accumulate on the bracket 8. It is ideal for the bracket to have a configuration with a minimum of unevenness so that it does not give a foreign body sensation. The bracket 8 shown in FIG. 5 is smoothly rounded as a whole. The orthodontic wire ligating member 2 can also have an external shape with a continuous smoothly curved configuration as a whole in conformity to the configuration of the bracket 8.

The leg portions 2*b* of the ligating member 2 are approximately in the shape of two English letter E's placed back to back in axial symmetry with respect to the back portion 2*a* as shown in FIG. 3. With this arrangement, the configuration of the wings 8*a* of the bracket 8 can be reduced in size. Accordingly, the leg portions 2*b* of the ligating member 2 are engaged with the lower portions 8*b* of the wings 8*a* in a compact form. Thus, the orthodontic wire ligating member 2 itself can be made compact in size. Because the outer surfaces of the bracket 8 are formed from curved surfaces, it is possible to provide a hygienic structure on which bits of food are unlikely to accumulate and which gives a minimal foreign body sensation in comparison to the conventional bracket structure.

Further, the bracket 8 has a continuous smoothly curved external configuration, which is also effective aesthetically. Further, because the ligating member 2 is made of a synthetic resin, it fits well to the bracket 8, which is made of a synthetic resin material similar to that of the ligating member 2. Further, because the ligating member 2 is a molded piece of a synthetic resin, various types of ligating members 2 having different structures can be molded relatively easily according to the mode of carrying out orthodontics. The back portion 2*a* and the wire keeper 2*c* of the ligating member 2 in the embodiment shown in FIG. 5 each have substantially the same structure and function as those in the foregoing embodiment.

As shown in FIG. 1, to carry out orthodontic treatment, the archwire 4 is inserted along the slot 5. The archwire 4 is positioned slightly below the upper surface of the groove 6 in the bracket 1. After the archwire 4 has been inserted into the slot 5, the ligating member 2 is inserted into the groove 6 of the bracket 1. The width and other dimensions of the ligating member 2 are conformable to the bracket 1 so that ligating member 2 can be inserted into the groove 6. Therefore, the ligating member 2 is inserted snugly into the groove 6 without an unnecessary gap.

Further pushing the ligating member 2 by continuously applying force thereto after it has been inserted into the groove 6 causes the leg portions 2*b* to be forced to extend along the outer peripheral surfaces of the wings 3 and thus fitted into the respective recesses in the lower portions 3*a* of the wings 3. The back portion 2*a* of the ligating member 2 is held between the wings 3 and secured to the upper surface of the groove 6, which is a recess of the bracket 1. The archwire 4 is retained without being pressed by the back portion 2*a*. This retaining structure allows the archwire 4 to be freely movable in the longitudinal direction (slot direction) while applying force to the surface of the slot 5 during the orthodontic treatment.

Figure 6:
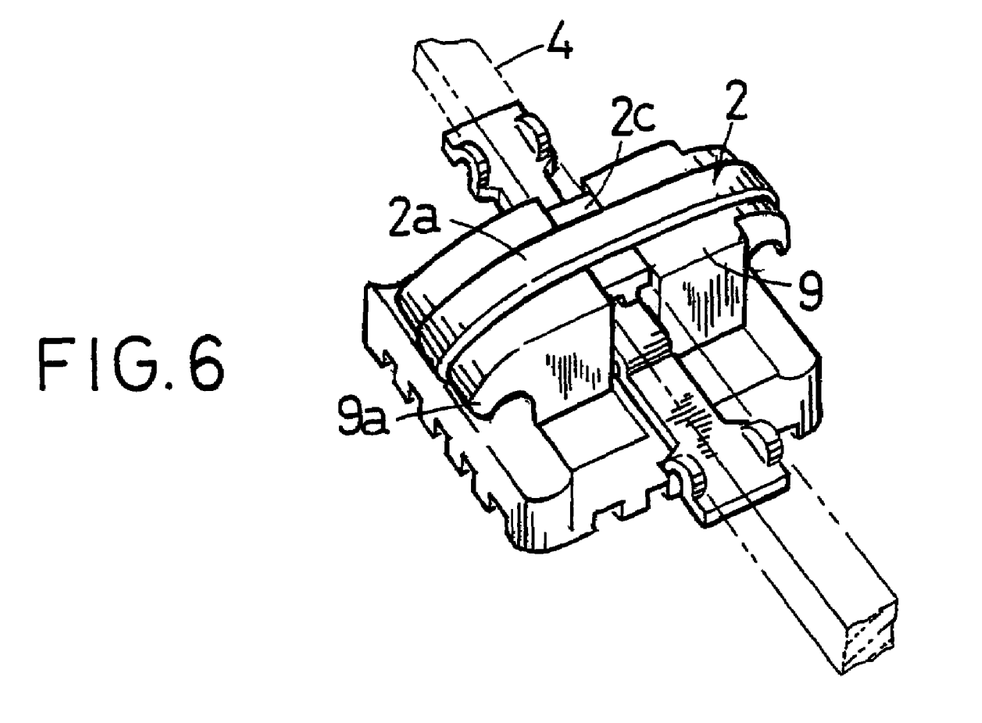
FIG. 6 is an external view showing an orthodontic wire ligating member according to a further embodiment of the present invention as applied to a single-type bracket.
Figure 7:
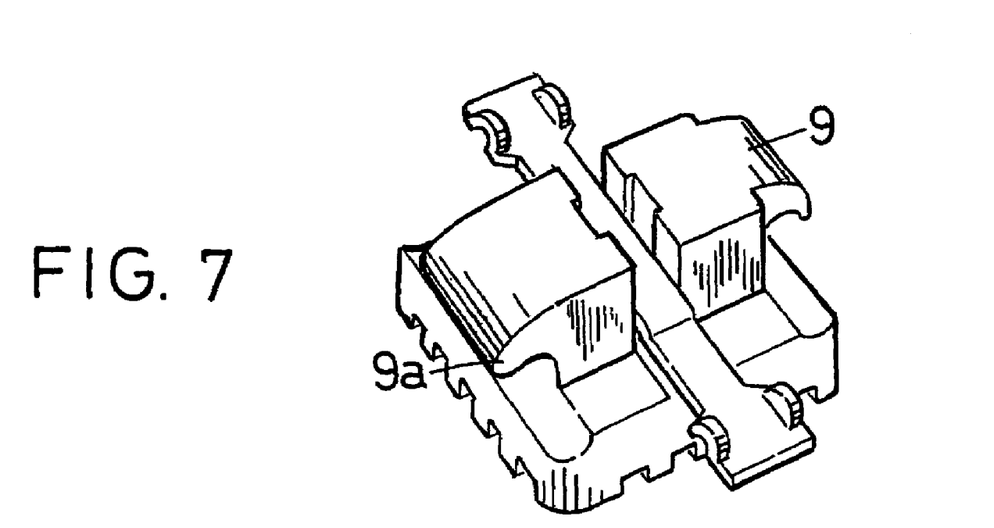
FIG. 7 is an external view showing the single-type bracket in the state of being a single element.

FIG. 6 is an external view of an orthodontic wire ligating member 2 according to a further embodiment of the present invention as applied to a single-type bracket 9 shown in FIG. 7. FIG. 7 shows the structure of the single-type bracket 9 in the state of being a single element. The single-type bracket 9 has a pair of wings 9*a* provided on both sides of the bracket body. The single-type bracket 9 has no recess, or groove, for positioning the back portion 2*a* of the ligating member 2 between the wings 9*a*. This ligating member 2 has a structure without leg portions 2*b* such as those shown in FIG. 3. The back portion 2*a* and the wire keeper 2*c* of the ligating member 2 shown in FIG. 6 each have substantially the same structure and function as those in the foregoing embodiment.

Figure 8:
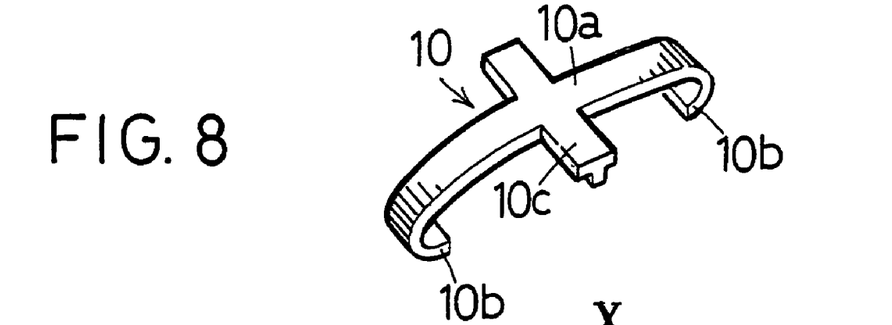
FIG. 8 is an external view of an orthodontic wire ligating member according to a further embodiment of the present invention, showing an example of an approximately I-shaped ligating member having leg portions equal in width to a back portion thereof.
Figure 9:
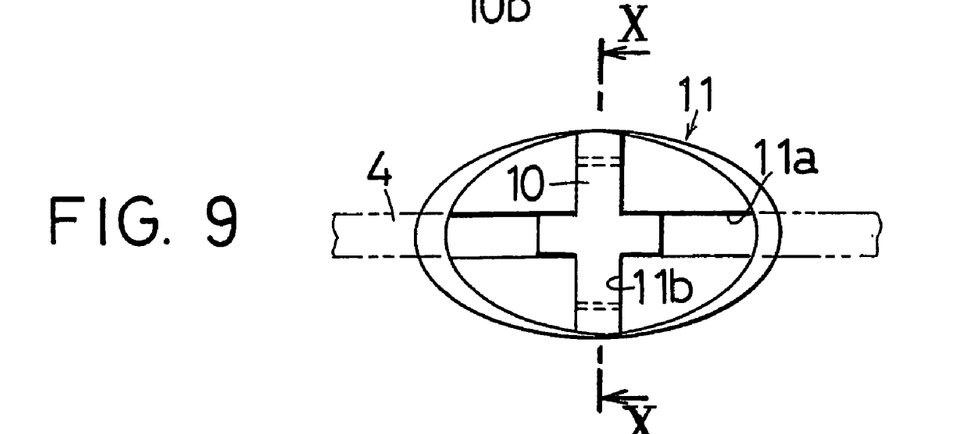
FIG. 9 is a front view of the approximately I-shaped orthodontic wire ligating member as applied to an elliptical bracket.
Figure 10:
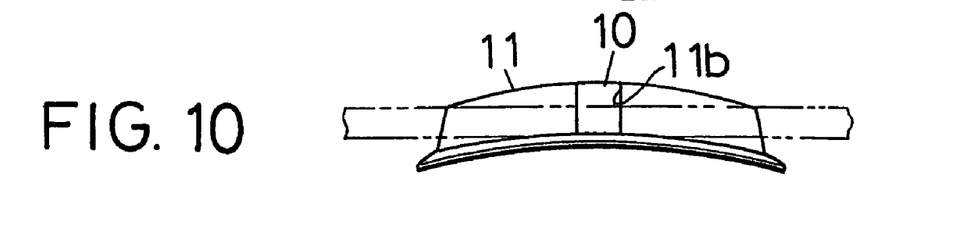
FIG. 10 is a side view of FIG. 9.
Figure 11:
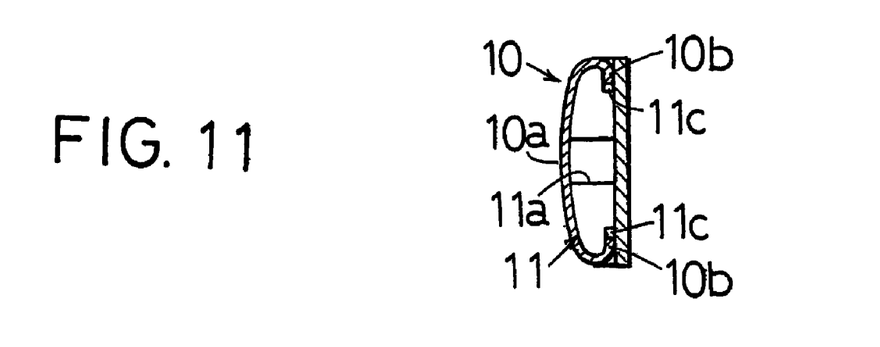
FIG. 11 is a sectional view taken along the line X—X in FIG. 9.

A ligating member 10 shown in FIG. 8 is similar to the ligating member 2 shown in FIG. 6 except that the upper surfaces of the back portion 2*a* and the wire keeper 2*c* are formed into the same curved surface. The back portion 10*a* and the wire keeper 10*c* of the ligating member 10 each have substantially the same structure and function as those in the foregoing embodiment. FIGS. 9 to 11 show a bracket having still another configuration. The leg portions 10*b* of the ligating member 10 shown in FIG. 8 do not have a portion projecting in the longitudinal direction of the archwire 4. The leg portions 10*b* are fitted into respective recesses or holes in an elliptical bracket 11 by an operation similar to the above.

The elliptical bracket 11 is elliptical as viewed in a direction perpendicular to the tooth surface. The bracket 11 may be circular instead of being elliptical. That is, it has a configuration defined by a closed curve. The elliptical bracket 11 is not provided with wings. The elliptical bracket 11 is provided with a slot 11*a* for installing the archwire 4 and a second groove 11*b* for retaining the ligating member 10. The second groove 11*b* extends in a direction crossing the slot 11*a*.

Grooves or holes 11*c* are provided in end portions of the elliptical bracket 11 at both ends of the second groove 11*b*. The back portion 10*a* of the ligating member 10 is arranged to be positioned slightly above the archwire 4 to retain it in the same way as the above. The leg portions 10*b* are fitted into the grooves or holes 11*c* of the elliptical bracket 11. When the ligating member 10 is in a ligating position, the upper surface of the back portion 10*a* of the ligating member 10 is flush with the surface of the elliptical bracket 11.

Figure 12:
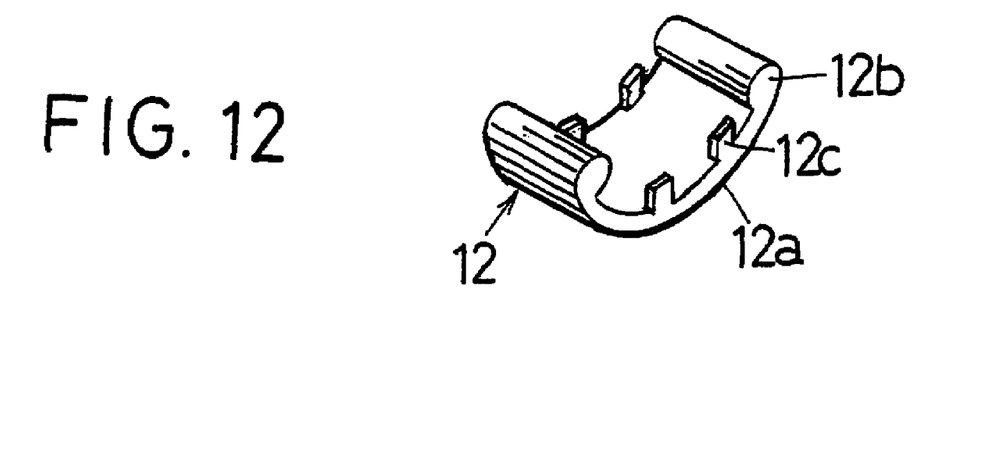
FIG. 12 is an external view of an orthodontic wire ligating member according to a further embodiment of the present invention, showing a modification of the approximately I-shaped ligating member having leg portions equal in width to a back portion thereof.

Accordingly, the orthodontic wire ligating member 10 can realize a smoothly curved external configuration as a whole. The curved surface configuration improves aesthetics and makes it unlikely that bits of food will adhere to the orthodontic appliances. Next, an orthodontic wire ligating member 12 having projections 12*c* provided on both sides of the back portion 12*a* as shown in FIG. 12 will be described as a further embodiment of the orthodontic wire ligating member according to the present invention. The ligating member 12 is applicable to the single-type bracket 9 shown in FIG. 7. The ligating member 12 can retain the archwire 4 on an existing single-type bracket without the need to provide recesses therein.

That is, when the ligating member 12 is fitted to the single-type bracket 9, the back portion 12*a* lies over the upper surface of the single-type bracket 9 in such a way that the projections 12*c* hold the single-type bracket 9 therebetween, and the leg portions 12*b* are fitted into the lower portions of the wings 9*a*. Thus, the ligating member 12 can retain the archwire 4 without displacement in the longitudinal direction of the archwire 4.

Figure 13:
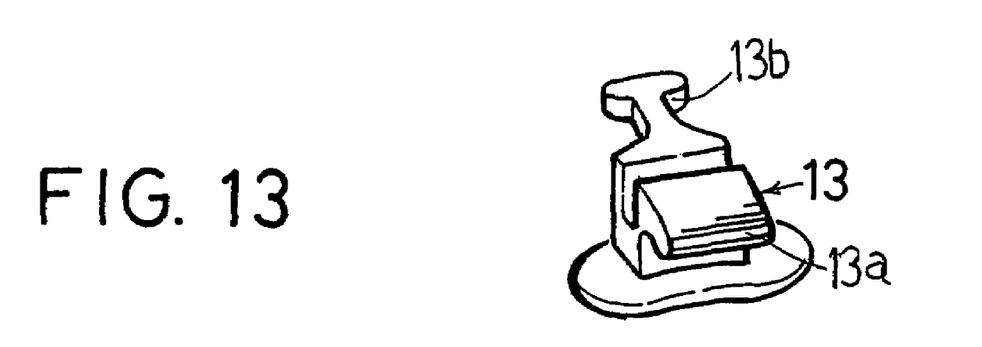
FIG. 13 is an external view showing a lingual bracket in the state of being a single element.
Figure 14:
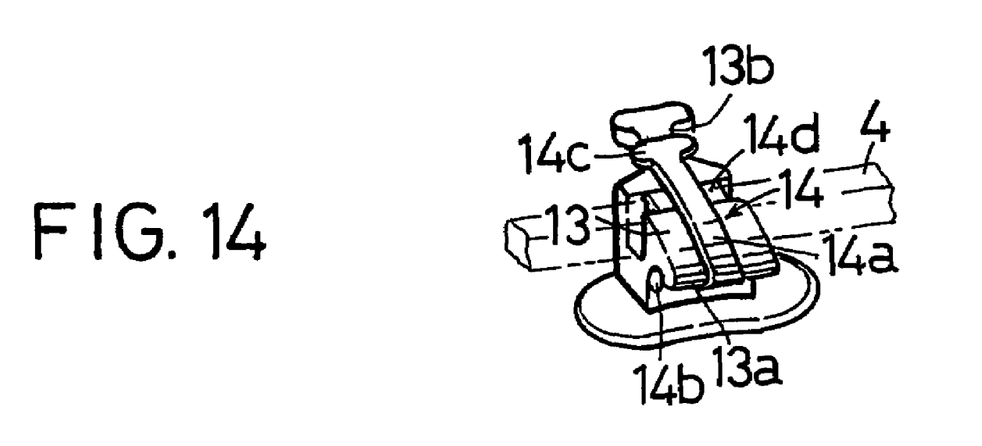
FIG. 14 is an external view showing an orthodontic wire ligating member according to a further embodiment of the present invention as applied to the lingual bracket.
Figure 15:
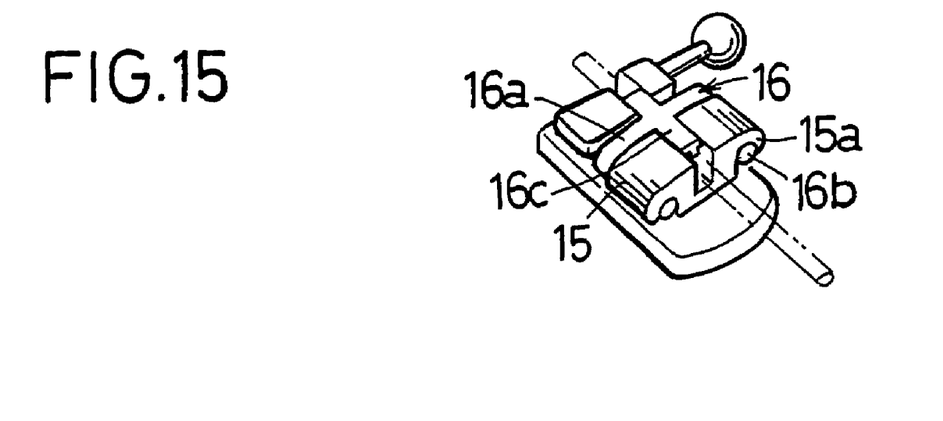
FIG. 15 is an external view showing an orthodontic wire ligating member according to a further embodiment of the present invention as applied to another lingual type of bracket.

FIGS. 14 and 15 show an example in which the orthodontic wire ligating member according to the present invention is applied to a lingual (tongue-side) bracket 13. The lingual bracket 13 shown in FIG. 13 is a publicly known bracket that is attached to the rear side of a tooth to perform orthodontic treatment. Because the lingual bracket 13 cannot be seen from the outside, it has the aesthetic advantage that the row of teeth wearing the lingual bracket 13 looks the same as an ordinary row of teeth. However, the lingual bracket 13 has the disadvantage that it is difficult to carry out orthodontic treatment. The orthodontic wire ligating member according to the present invention is also applicable to the orthodontic method using the lingual bracket 13. FIG. 13 shows the external appearance of the lingual bracket 13 in the state of being a single element. A special-purpose ligating member 14 is mounted on a wing 13a of the lingual bracket 13, and the resulting orthodontic system is used as shown in FIG. 14.

A leg portion 14b of the ligating member 14 is fitted into the wing 13a. The back portion 14a is placed over the upper surface of the lingual bracket 13. Further, a leg portion 14c on the opposite side is fitted to and engaged with a neck portion 13b of the lingual bracket 13, thereby retaining an archwire 4. The wire keeper 14d has substantially the same structure and function as those in the foregoing embodiment. FIG. 15 shows a lingual bracket 15 for premolars. A ligating member 16 can be mounted on the lingual bracket 15 with an arrangement similar to the above. A leg portion 16b of the ligating member 16 is engaged with each wing 15a of the lingual bracket 15, thereby allowing the ligating member 16 to be mounted on the lingual bracket 15. The back portion 16a and the wire keeper 16c of the ligating member 16 each have substantially the same structure and function as those in the foregoing embodiment.

Figure 16:
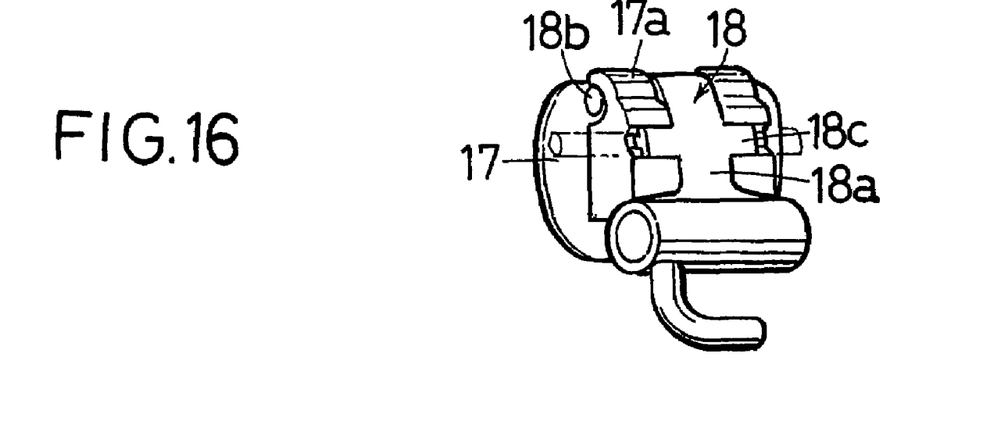
FIG. 16 is an external view showing an orthodontic wire ligating member according to a further embodiment of the present invention as applied to a buccal tube.
Figure 17:
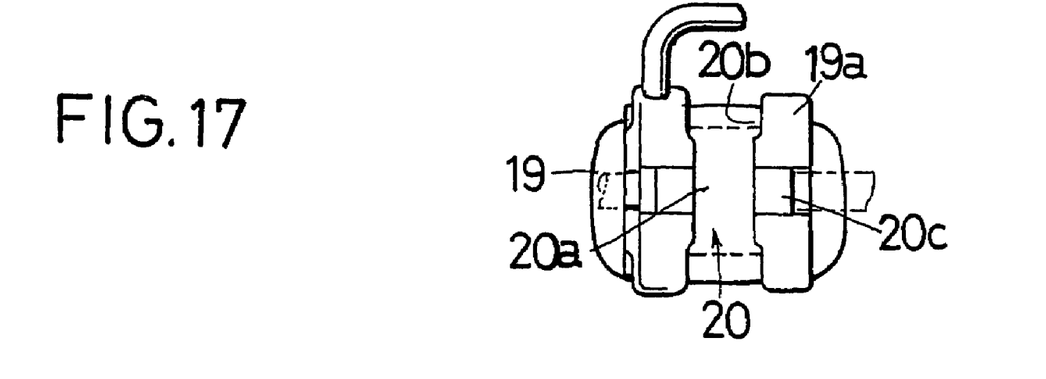
FIG. 17 is an external view showing an orthodontic wire ligating member according to a further embodiment of the present invention as applied to a bracket with fook.

FIGS. 16 and 17 show examples in which the orthodontic wire ligating member according to the present invention is applied to tubes for molars. FIG. 16 shows a double convertible tube 17. The tube 17 is of the type that allows two wires to pass therethrough. In this embodiment, a ligating member 18 is placed over the upper surface of the tube 17, and a leg portion 18b of the ligating member 18 is fitted to a wing 17a of the tube 17, in the same way as the above. The back portion 18a and the wire keeper 18c of the ligating member 18 each have substantially the same structure as that in the foregoing embodiment.

A bracket with fook 19 shown in FIG. 17 is a single convertible tube. In this type of tube also, a ligating member 20 is fitted over the upper surface of the bracket 19, and a back portion 20a and a wire keeper 20c of the ligating member 20 are inserted into groove and slot, and a leg portion 20b of the ligating member 20 is fitted to a wing 19a of the bracket 19, thereby securing the ligating member 20 to the bracket 19. As the bracket 19, if a standard type tube having a wing is available, it is used. If such a tube is unavailable, a tube provided with a portion for engagement with the ligating member 20 is prepared. The back portion 20a and the wire keeper 20c of the ligating member 20 each have substantially the same structure as that in the foregoing embodiment.

[Operation/working-Effect of Embodiments]

The operation/working-effect of the embodiments detailed above may be summarized as follows. The wire securing methods using the conventional ligating members are complicated and require the orthodontist to have highly proficient skill in ligating. In contrast, the orthodontic wire ligating member according to any of the embodiments of the present invention enables the treatment to be finished in a reduced period of time and moreover allows orthodontic pain inflicted on the patient to be reduced to a considerable extent. The bracket configuration is not restricted to the conventional ones. However, the use of an optimal bracket configuration conformable to the ligating members according to the embodiments enables the effect of the orthodontic treatment to be improved furthermore.

Existing conventional devices capable of manifesting an effective corrective force when used for tooth movement are designed on the assumption that an archwire, an elastic chain, a coil spring, or the like operates with a force of at least about 0.59 to 0.69 N (Newton) per tooth. To manifest the force for orthodontic correction with a conventional device, for example, an archwire of nickel-titanium alloy for orthodontics that has a minimum diameter of about 0.36 mm is generally used. Further, a polyurethane elastic chain that is used in engagement with a bracket to partially supplement the corrective force is generally required to have a minimum thickness of about 0.4 mm.

In this regard, the devices according to the embodiments of the present invention allow orthodontics to be effected with an archwire of nickel-titanium alloy for orthodontics that has a smaller diameter than in the conventional devices, i.e. 0.25 mm (±0.02 mm) or 0.3 mm (±0.02 mm). Regarding polyurethane elastic chains, orthodontics can be effected with an elastic chain having a thickness of approximately 0.2 mm or 0.3 mm. That is, the embodiments of the present invention provide treatment systems that allow the orthodontics to be completed in a reduced period of time and permit the orthodontic pain inflicted on the patient to be reduced in comparison to the conventional devices, as will be understood from the sizes of the archwire and the elastic chain.

The effect of the systems according to the embodiments of the present invention is particularly remarkably manifested in leveling in the initial stage of orthodontic treatment. A clinical trial example shows that the tooth movement can be effected at a speed approximately two times higher than in the past. Moreover, although the conventional orthodontic methods cause most patients to feel a pain, the embodiments of the present invention minimize the pain inflicted on the patient because the tooth movement can be effected with a smaller corrective force than in the past. According to clinical trial examples carried out by the present inventors, the rate of the number of patients who complained of a pain was approximately 10%.

Further, because the archwire is installed along a row of teeth, the direction of the slot in each bracket is coincident with the direction of the row of teeth. The brackets are fitted along the direction of the row of teeth smoothly with minimal unevenness. Therefore, the resulting orthodontic system is easy to clean, and it is unlikely that bits of food will be left thereon. Accordingly, it is possible to realize clean orthodontic treatment in comparison to the past. Further, because the size of the bracket can be reduced, the bracket itself can be made compact, and it is possible to obtain a structure excellent in aesthetics as well. Although the embodiments of the present invention have been described above, the specific structure of the present invention is not necessarily limited to the embodiments, as a matter of course.

What is claimed is:

1. An orthodontic wire ligating member engageable with an orthodontic bracket to retain an archwire inserted into a slot in said bracket, said ligating member being an elastically deformable member made of a synthetic resin and comprising:

at least two spaced leg portions detachably engageable with said bracket; and a back portion integral with said at least two leg portions and elastically deformable flexibly to engage said bracket, and to retain the archwire of said bracket, wherein said back portion has a wire keeper formed integral with said back portion and inserted into the slot to hold the archwire of said bracket, wherein a spacing between said wire keeper and the archwire is adjusted by varying a thickness of said wire keeper, wherein said leg portions are provided with projections extending along a longitudinal direction of the archwire, said projections being engageable with respective recessed portions formed in lower portions of wings that project from said bracket, wherein said leg portions are disposed on both ends of the back portion and are shaped to be mirror images of each other, and wherein said wire keeper comprises a bottom surface and a top surface, said bottom surface being smaller in surface area than said top surface.

2. The orthodontic wire ligating member according to claim 1, wherein said synthetic resin is at least one selected from the group consisting of polyamides, polyacetals, and polycarbonates, and has a tensile break strength of not less than 55 MPa, a bending strength of not less than 80 MPa, a modulus in flexure of not less than 2500 MPa and an impact value of not less than 50 J/m.

3. The orthodontic wire ligating member according to claim 1, wherein said back portion and said wire keeper has a continuously smooth and curved external shape in conformity with surface configuration of said bracket.

4. The orthodontic wire ligating member according to claim 3, wherein said ligating member is engageable with said orthodontic bracket which is elliptical as viewed in a direction normal to the joint surface to be bonded to a tooth surface.

5. The orthodontic wire ligating member according to claim 1, having a shape which allows orthodontics to be effected with an archwire having a diameter of from 0.20 mm to 0.35 mm.

6. The orthodontic wire ligating member according to claim 5, wherein the shape allows for orthodontics to be effected with a polyurethane elastic chain having a wall thickness of from 0.2 mm to 0.3 mm, said polyurethane elastic chain to be engaged with said bracket.

* * * * *